(12) United States Patent
Boukanov et al.

(10) Patent No.: US 6,762,337 B2
(45) Date of Patent: Jul. 13, 2004

(54) PRESSURE BANDAGES FOR WOUNDS

(76) Inventors: Stanley Boukanov, 4800 Lexington Ave., Beltsville, MD (US) 20705; Mikhail Boukanov, 4800 Lexington Ave., Beltsville, MD (US) 20705

(*) Notice: Subject to any disclaimer, the term of this patent is extended or adjusted under 35 U.S.C. 154(b) by 227 days.

(21) Appl. No.: 10/053,692

(22) Filed: Jan. 24, 2002

(65) Prior Publication Data

US 2003/0139696 A1 Jul. 24, 2003

(51) Int. Cl.[7] ................................................. A61F 13/00
(52) U.S. Cl. ............................ 602/53; 602/41; 602/42; 602/60
(58) Field of Search ......................... 606/201, 202; 602/41–59, 60, 61, 62, 63, 75, 79, 19

(56) References Cited

U.S. PATENT DOCUMENTS

| | | | |
|---|---|---|---|
| 1,646,590 A | 10/1927 | Mildenberg | |
| 2,823,668 A | 2/1958 | Van Court et al. | |
| 3,561,442 A | 2/1971 | Goswitz | |
| 3,570,495 A | 3/1971 | Wright | |
| 3,933,150 A | 1/1976 | Kaplan et al. | |
| 4,135,503 A | 1/1979 | Romano | |
| 4,360,351 A | * 11/1982 | Travinski | ............. 441/94 |
| 4,635,635 A | 1/1987 | Robinette-Lehman | |
| 5,392,782 A | 2/1995 | Garrett | |
| 5,500,952 A | * 3/1996 | Keyes | ............. 2/465 |
| 5,507,721 A | 4/1996 | Shippert | |
| 5,527,270 A | 6/1996 | Chase et al. | |
| 5,628,723 A | 5/1997 | Grau | |
| 5,643,315 A | * 7/1997 | Daneshvar | ............. 606/201 |
| 5,746,213 A | * 5/1998 | Marks | ............. 600/499 |
| 5,843,018 A | 12/1998 | Shesol et al. | |
| 6,171,271 B1 | 1/2001 | Hornberg | |
| 6,331,170 B1 | * 12/2001 | Ordway | ............. 602/19 |

* cited by examiner

Primary Examiner—Kim M. Lewis
(74) Attorney, Agent, or Firm—Richard C. Litman

(57) ABSTRACT

A series of pressure bandages for wounds in a packaged and hermetically sealed form. A first embodiment has an inflatable linear hollow pressure bandage having one or more sterile bandages freely attached to a mounting strip and with an adhesive strip at one end for initial application. Hook and loop fastening is provided for final attachment. In all the embodiments a carbon dioxide gas and the like gas containing miniature tank with a valve is provided for inflating the bandage on site to apply pressure to the bleeding wound to minimize the loss of blood. A second embodiment is a rectangular pressure bandage lacking any fastening straps. A third embodiment is cone-shaped for maintaining containing pressure on a severed or nearly-severed limb. A fourth embodiment is dome-shaped with a pair of straps for applying on a head wound.

4 Claims, 7 Drawing Sheets

PRESSURE BANDAGES FOR WOUNDS

BACKGROUND OF THE INVENTION

1. Field of the Invention

The present invention relates generally to medical bandages. More specifically, the invention is a packaged and hermetically sealed, inflatable bandage in the form of a linear hollow cuff as a first embodiment having one or more sterile dressings freely attached to a mounting strip and with an adhesive strip at one end for initial application by the injured or a medic. Hook and loop fastening is provided for final attachment of the pressure bandage on the injury. A carbon dioxide gas container with an inlet valve is provided for inflating the bandage on-site. Other embodiments are in the form of a conical pressure bandage or a skull cap bandage.

2. Description of the Related Art

The related art of interest describes various bandages, but none discloses the present invention. There is a need for an economical bandage which is versatile in application to single or double puncture wounds, e.g., bullet wound passing through an arm, leg, etc.) of the human body which can be carried by the injured (such as a military person) for self-application to prevent the excessive loss of blood from a wound. The relevant art will be discussed in the order of perceived relevance to the present invention.

U.S. Pat. No. 5,628,723 issued on May 13, 1997, to Bernard Grau describes an emergency bandage comprising a sterile dressing attached to a web portion having a first pressure enhancement member (with 12 embodiments) and at least one gapped wrapping element (hooking dowel) for application to an injured arm or leg. A second pressure enhancement member can have a rectangular platform having four U-shaped wrapping stubs attached around a central stub on top and parallel elongated bars on the bottom surface.

U.S. Pat. No. 4,635,635 issued on Jan. 13, 1987, to Cynthia Robinette-Lehman describes an arcuate shaped tourniquet cuff having a hook and loop attachment means and a secondary ribbon attachment means at one end. An enclosed bladder is inflated with an external inflation means by two tubes having male connectors.

U.S. Pat. No. 5,507,721 issued on Apr. 16, 1996, to Ronald D. Shippert describes an arm wound dressing having a rectangular compressed dressing pad that expands as it absorbs body fluid and a rectangular backing member with hook or loop fastener strips, and two long straps with loop or hook fastener strips that increases pressure up to 0.4 psi.

U.S. Pat. No. 6,171,271 issued on Jan. 9, 2001, to Irene Hornebert describes a rectangular hip joint or girdle pressure bandage having a pressure bladder for filling with fluid and fastening with hook and loop fastening strips on opposite edges.

U.S. Pat. No. 5,843,018 issued on Dec. 1, 1998, to Barry F. Shesol et al. describes a disposable sterile emollient carrier device comprising a rectangular stretchable bandage having a bonded or movable emollient carrier platform. The platform can be either a medical grade foam sheeting surface or a porous mesh pocket. A releasable hook fastener strip is positioned at one end of the device or pressure sensitive tape can be used. The device with different configurations can be used around a finger, palm, arm, and chest.

U.S. Pat. No. 1,646,590 issued on Oct. 25, 1927, to Julius Mildenberg describes a rectangular massage bandage comprising a belt-shaped body having a pneumatic band inflated by the patient by mouth via a tube and mouthpiece valve. Rods, slats or blocks are added to the body as stiffening aids. Straps and buckles are added to the belt.

U.S. Pat. No. 2,823,668 issued on Feb. 18, 1958, to Carl P. Van Court et al. describes an inflatable arm splint comprising a rectangular outer wrapping having end fasteners and side hooks, an inner gauze or cloth wrapper, a plurality of parallel stays and fluid chambers, and a tube connected to a pressure gauge and an air pressure applying bulb having a check valve.

U.S. Pat. No. 3,570,495 issued on Mar. 16, 1971, to Frank O. Wright describes a longitudinal pneumatic tourniquet for constricting a person's limb comprising a flexible cover containing an air bladder fillable by an intake tube with a check valve. The tourniquet has hook and loop regions for strapping the tourniquet on the limb.

U.S. Pat. No. 3,933,150 issued on January 1976, to Burton H. Kaplan et al. describes a medical pneumatic trouser for emergency autotranfusion comprising a single piece, double-walled flexible panel forming a chamber for receiving pressurized air. The pair of lower sections surround the legs and are strapped by hook and loop fastening strips.

U.S. Pat. No. 4,135,503 issued on Jan. 23, 1979, to Nicholas A. Romano describes an orthopedic device to provide ambulatory traction to specific levels of the spine. A hand inflatable bladder is positioned between a rigid base plate and an apertured template plate, and mounted on a latex belt with straps and buckles. An air inflatable bulb with a release valve is attached to the bladder.

U.S. Pat. No. 5,392,782 issued on Feb. 28, 1995, to John R. Garrett describes a disposable rectangular medical pressure cuff comprising a plastic sheet and a woven fabric sheet which are heat sealed with inflation fittings to form a bladder and attached to the body by hook and loop fastening.

U.S. Pat. No. 3,561,442 issued on Feb. 9, 1971, to John T. Goswitz describes a mastectomy compression bandage having a rectangular shape with a half of the bandage being elastic and the other half being non-elastic and having a breast cup. Elastic and non-elastic straps are provided to hold a bandage over the mastectomy area.

U.S. Pat. No. 5,527,270 issued on Jun. 18, 1996, to Beverly J. Chase et al. describes a mastectomy bandage comprising a main body panel of a non-elastic breathable fabric and an elastic panel portion to be positioned by shoulder straps and fastened by hook and loop fastening.

None of the above inventions and patents, taken either singularly or in combination, is seen to describe the instant invention as claimed. Thus, a pressure bandage for wounds, especially solving the aforementioned problems for double puncture wounds and head wounds, is desired.

SUMMARY OF THE INVENTION

The invention is a packaged and hermetically sealed, inflatable linear hollow bandage cuff as a first embodiment having one or more sterile dressings freely attached to a linear mounting strip and with an adhesive strip at one end for initial application. Hook and loop fastening is provided for final attachment by a single strap. A carbon dioxide gas container with an inlet valve is provided for inflating the bandage on site to apply pressure to the bleeding wound to minimize the loss of blood. A second embodiment is a rectangular pressure bandage for injured limbs and body and lacks any fastening straps. A third embodiment pressure bandage has a cone shape having two fastening straps for containing a nearly severed appendage and lacks a mounting strip. A fourth embodiment is a dome-shaped pressure bandage for an injured head.

Accordingly, it is a principal object of the invention to provide a hermetically sealed bandage package with an integrated gas tank for suppressing bleeding of wounds and applicable by the wounded.

It is another object of the invention to provide a first embodiment of a rectangular pressure bandage having one or more sliding bandages on an internal holding strip and one external fastening strap.

It is a further object of the invention to provide a second embodiment of a rectangular pressure bandage lacking any fastening straps.

Still another object of the invention is to provide a third embodiment of a pressure bandage which is cone-shaped and has two fastening straps for maintaining contact between two severable or severed body parts.

Yet another further object of the invention to provide a fourth embodiment of a pressure bandage which is dome-shaped for head injuries and having two fastening straps.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed to an assortment of pressure bandages which are prepackaged in sterile packets in a rolled condition for immediate use by either the injured or by a medical practitioner such as a medic in battle. Some of the pressure bandages have an adhesive applied edge for positioning proximate the wound and then extending the pressure bandage over the wound. The pressure bandages come in an assortment of shapes and sizes for application on appendage wounds, e.g., finger, ear, head, hand, arm, feet, and leg. Some pressure bandages of the present invention have tethers or straps with hook and loop fastening straps for securing the pressure bandage to the wound. All the pressure bandages have a pressurized gas container securely attached to the bladder for inflating the bladder.

Figure 1:
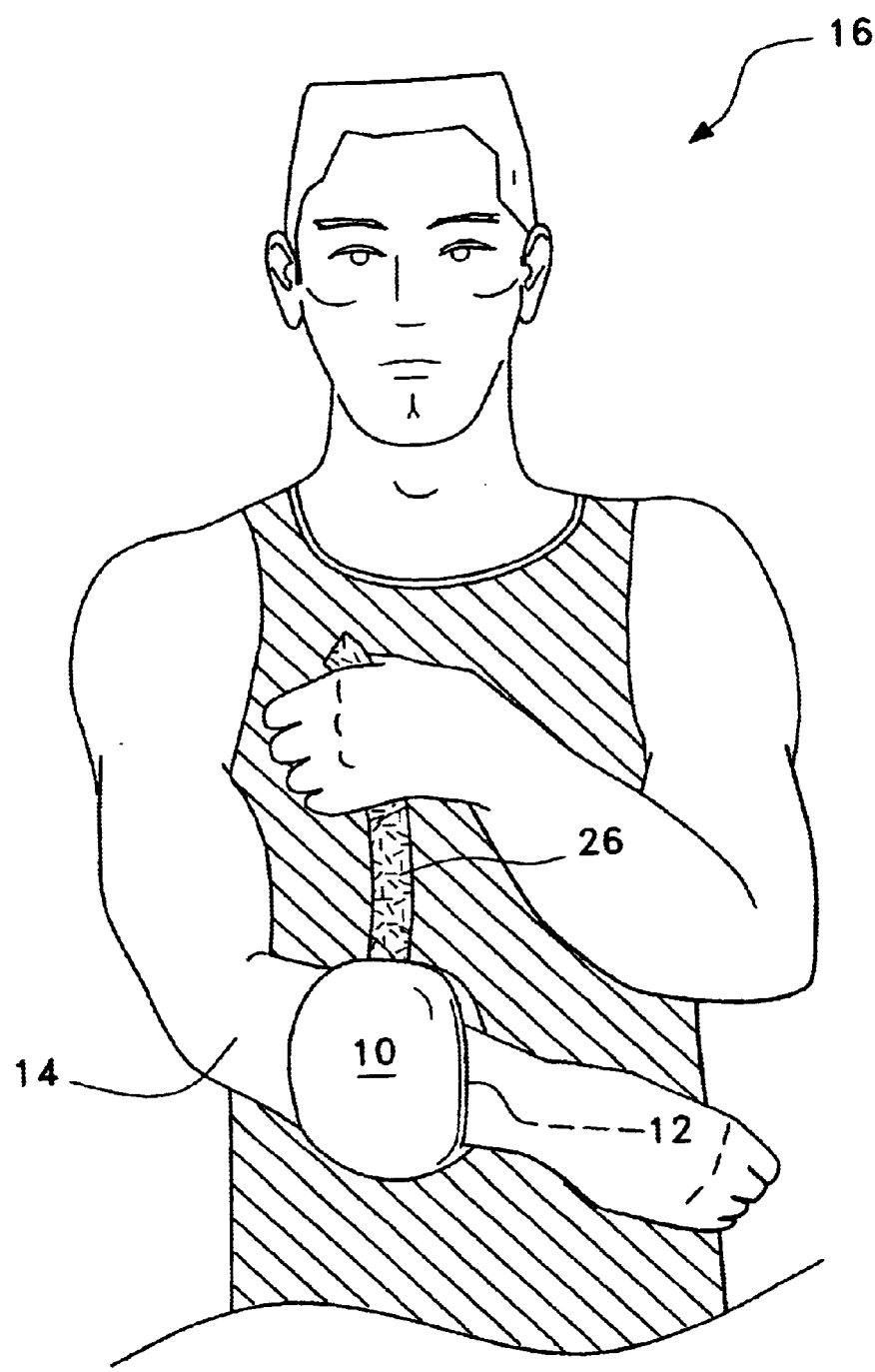
FIG. 1 is an environmental, perspective view of a pressure bandage for a forearm wound being applied by the injured person according to the present invention.

In FIG. 1 a first embodiment of the present invention for an elliptically shaped pressure bandage 10 is being applied to a double wound 12 caused by a bullet passing through the forearm 14 by an injured person 16. The pressure bandage 10 is initially rolled up in a sterile package with instructions on how to use (not shown).

Figure 2:
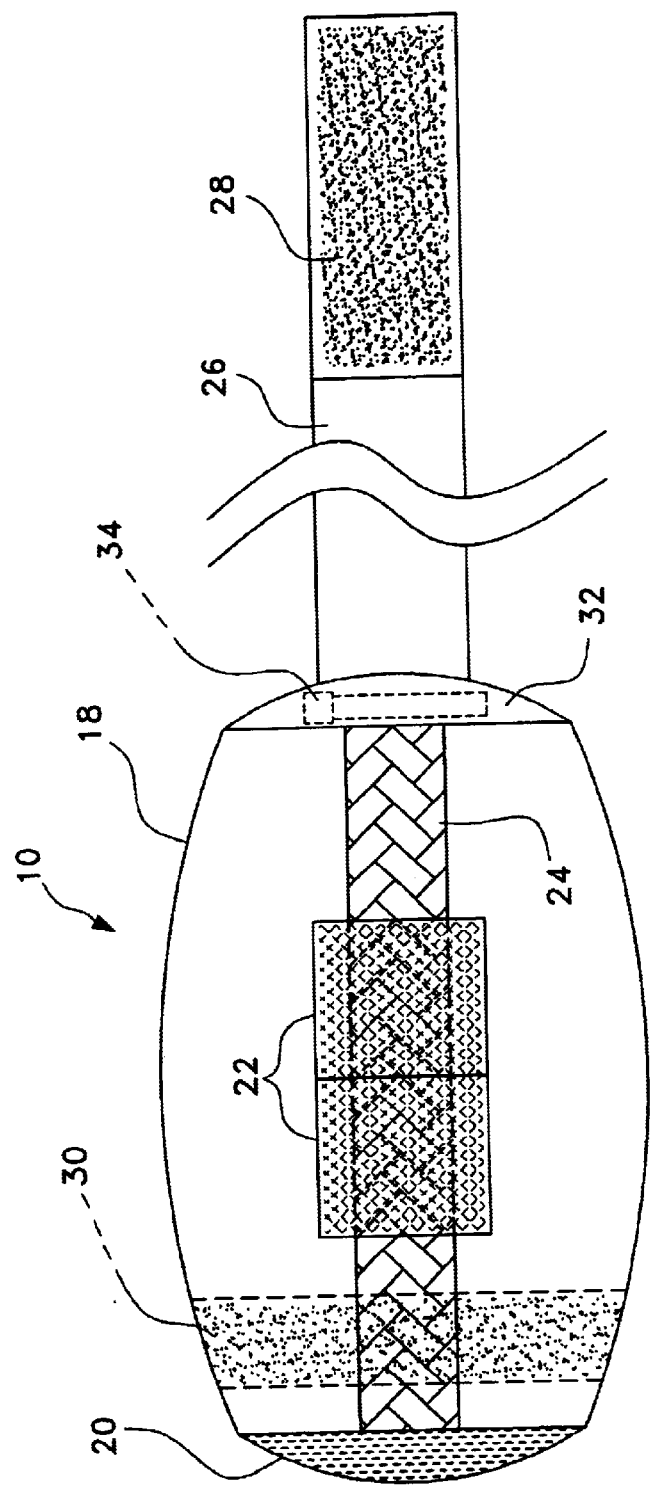
FIG. 2 is a plan view of the inner surface of the pressure bandage of FIG. 1 as a first embodiment having a sliding bandage portion.

As illustrated in FIG. 2 as an inside view, the pressure bandage 10 is formed from a flexible elliptically shaped bladder 18 which is positioned on the separate wounds 12 by attaching the adhesive strip 20 proximate one of the puncture wounds as an anchoring device. The adhesive strip 20 can be initially covered by a conventional non-adhesive strip (not shown). One or two sterile gauze dressings 22 are wrapped around a plastic strip 24 for exact placement on the bullet holes. A strap 26 extends from one edge of the pressure bandage 10 and has an extended patch of loop fastening material 28 on the inside or front surface. The hook fastening material patch 30 is attached to the outside or rear surface as shown of the pressure bandage 10 for securing the pressure bandage around the forearm 14. On the end of the elliptical pressure bandage 10 with the hook strap 26, a pouch 32 is provided for securing the pressurized gas cartridge 34.

Figure 3:
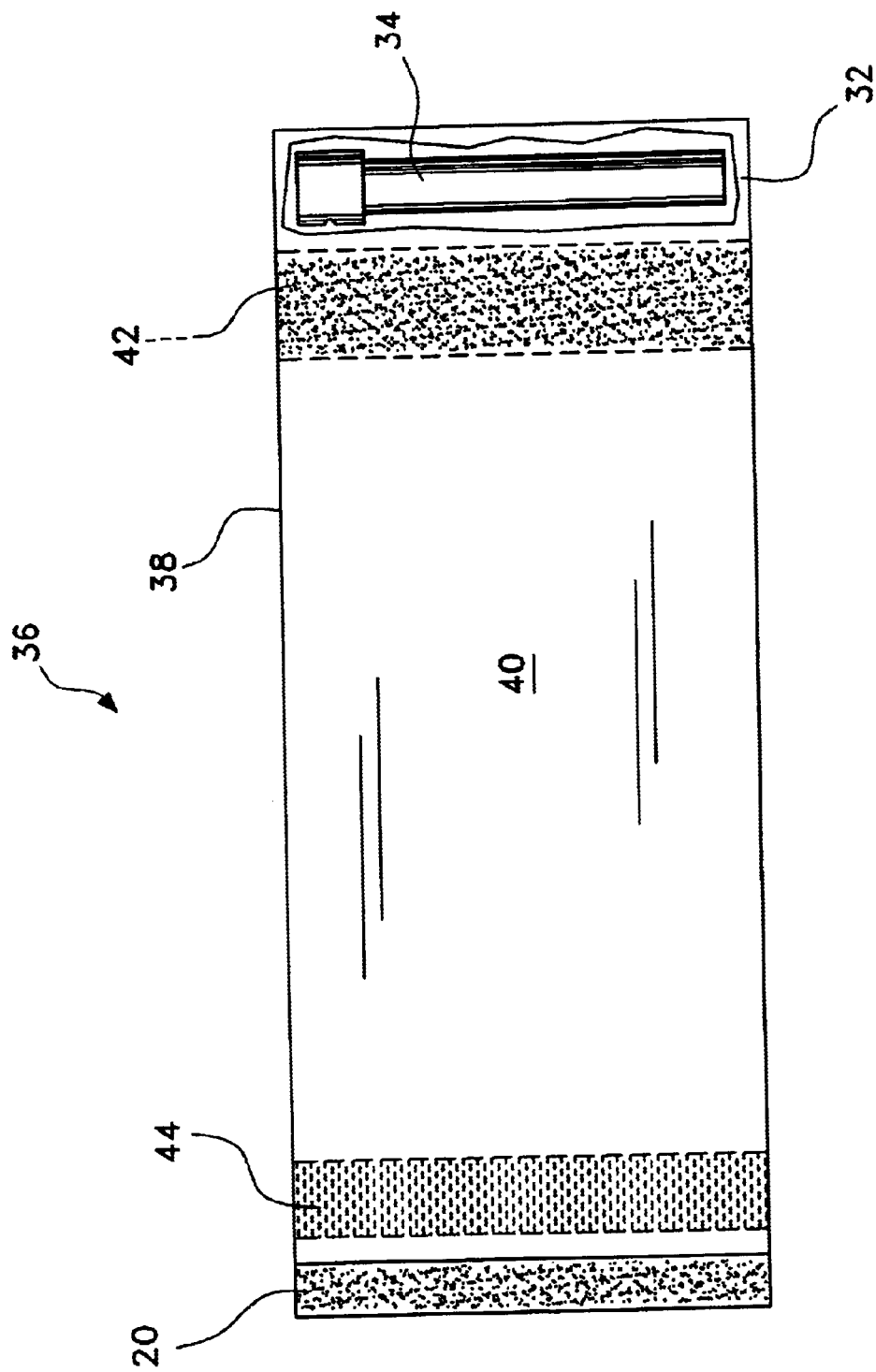
FIG. 3 is a plan view of the outer surface of a second embodiment of the pressure bandage omitting the sliding bandage aspect and any attachment straps.

FIG. 3 illustrates a second embodiment of the present invention in an outer surface view as a rectangular pressure bandage 36 having a rectangular bladder 38 in a pouch 32 (shown partially broken away) having the pressurized gas cartridge 34 at one end with the adhesive strip 20 at the opposite end. The hidden rectangular sterile gauze dressing 40 positioned on the opposite inner surface is extensive in area and extends from the adhesive strip 20 to the cartridge pouch 32. The hook fastening strip 42 on the inner side attaches to the loop fastening strip 44 on the outer side. This embodiment has the advantage of not requiring any further strapping for further securement of the pressure bandage 36.

Figure 4:
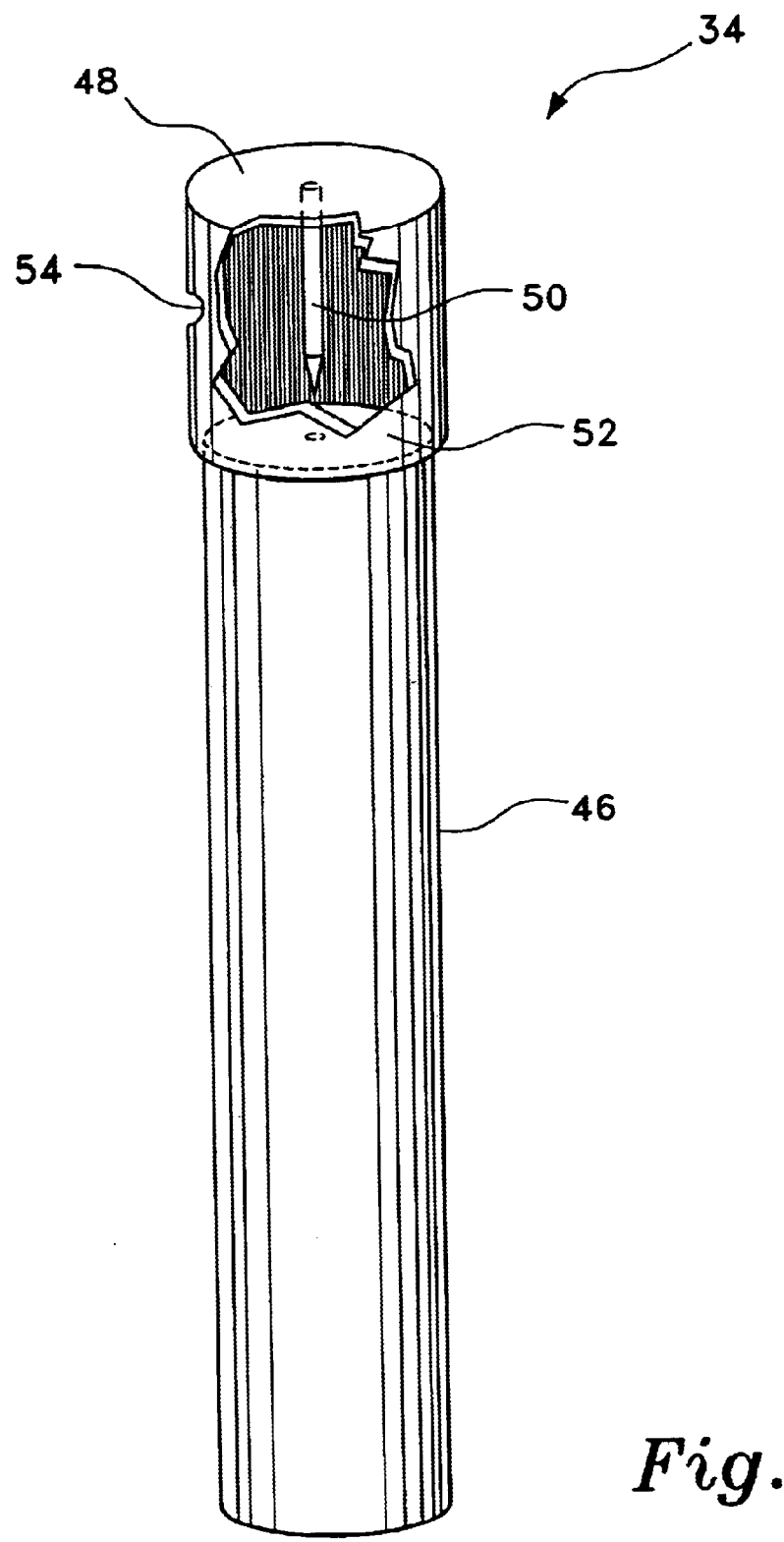
FIG. 4 is a perspective view of a carbon dioxide supply cartridge with its cap partially broken to show the puncturing needle and the nozzle used in all the embodiments.

A shown in FIG. 4 a carbon dioxide gas as an example is stored under pressure in the gas cartridge 34 having a capacity of 1–3 ml. A long cylindrical gas tank body 46 has a cap 48 with a slightly larger inside diameter as the outside diameter of the tank body 46 to enable depression of the cap 48 with its internal pin 50 to penetrate the top portion 52 to release the pressurized gas to exit through a nozzle aperture 54 on the side of the cap 48.

Figure 5:
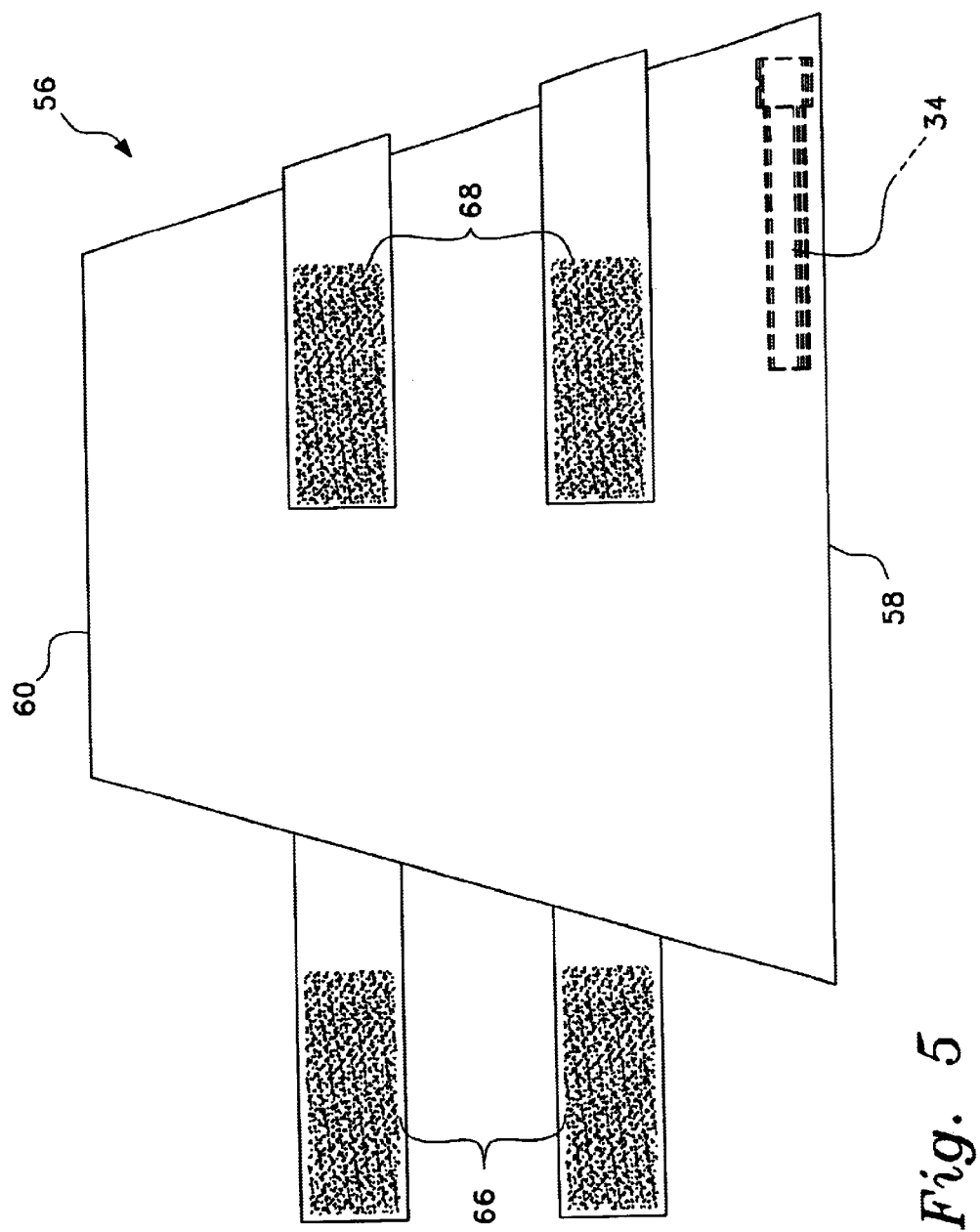
FIG. 5 is an elevational front view of a truncated cone-shaped pressure bandage as a third embodiment having four fastening straps.
Figure 6:
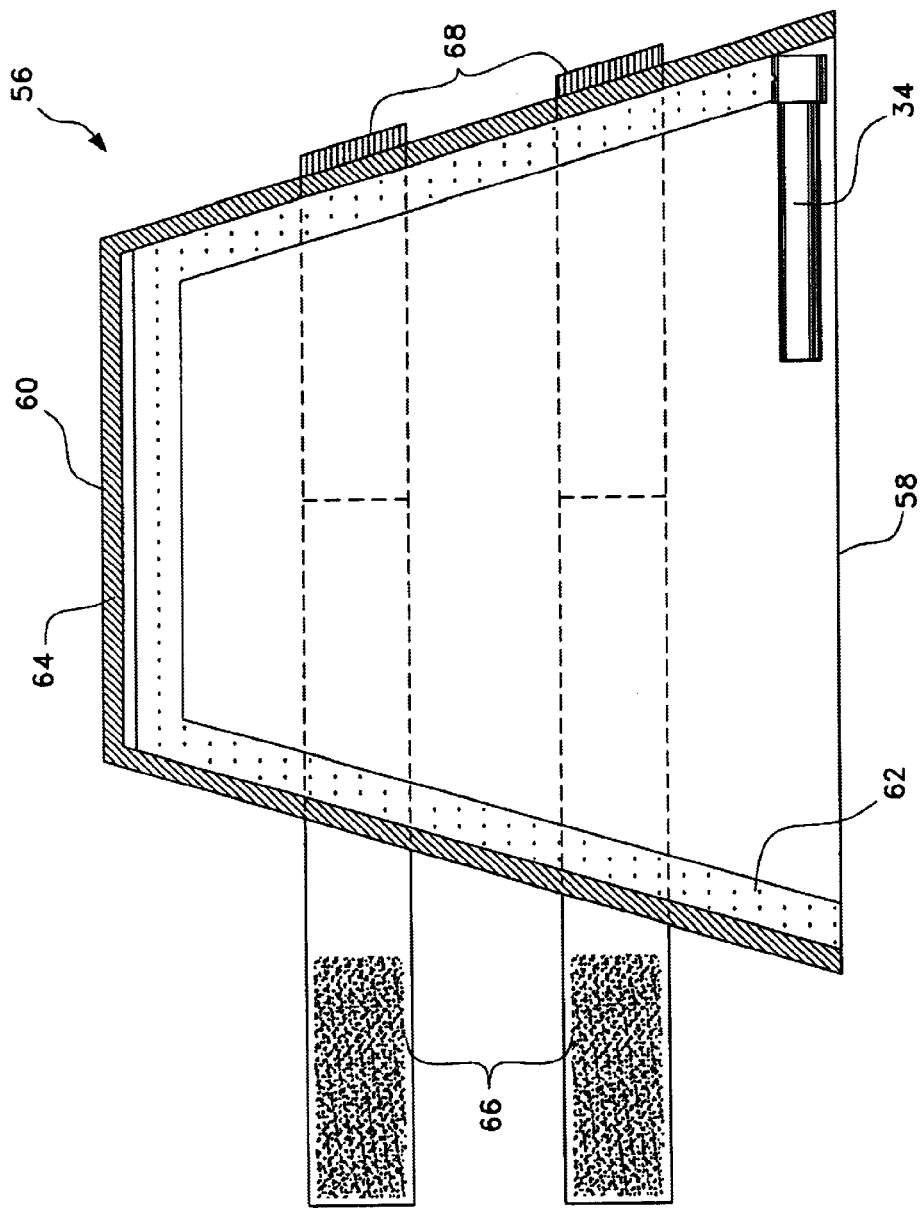
FIG. 6 is a cross-sectional view of FIG. 5 embodiment of the truncated cone-shaped pressure bandage.

Attention is now directed to the third embodiment of a truncated cone-shaped pressure bandage 56 depicted in FIGS. 5 and 6, with an open bottom 58 and a closed top 60 which is used for containing a severed or almost severed appendage such as a hand or foot. The gauze bandage 62 is located as a liner on the inside adjacent the truncated cone-shaped bladder 64. The gas cartridge 34 is located at the bottom edge. A pair of extended hook fastener straps 66 are provided to attach to the loop fastener patches 68 adhesively attached flat on the bladder 64 to secure the pressure bandage 56 to the injury area.

Figure 7:
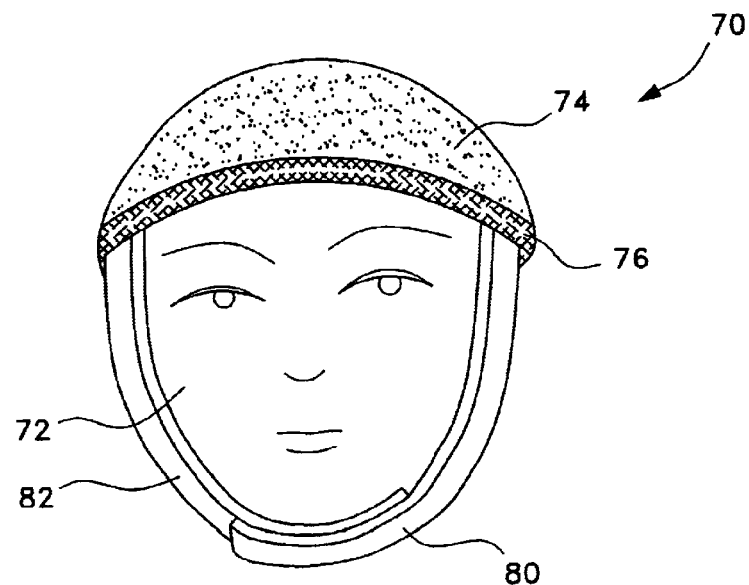
FIG. 7 is an environmental front elevational view of a fourth embodiment of a pressure bandage having a dome shape attached to an injured person's head by two fastening straps.
Figure 8:
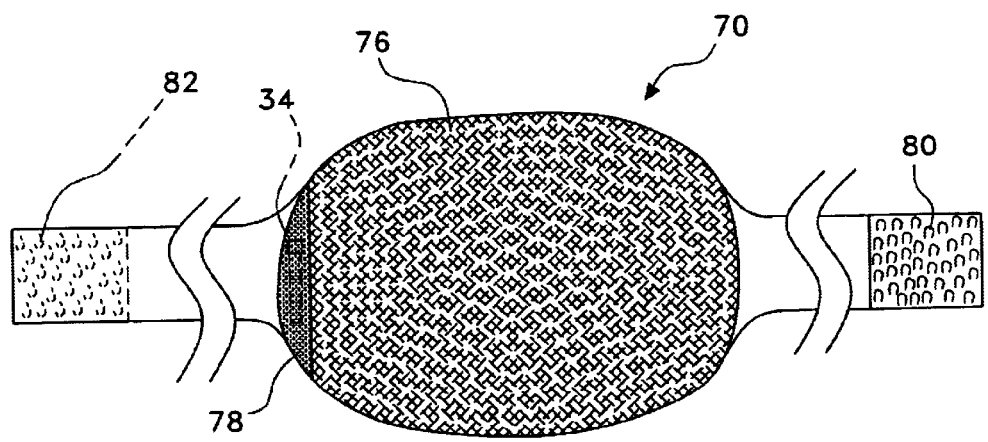
FIG. 8 is a partial bottom view of the inside surface of the FIG. 7 embodiment of the pressure bandage.

The last and fourth embodiment shown in FIGS. 7 and 8 is a dome-shaped pressure bandage 70 secured to a person 72 with a head injury. The bladder 74 has a coextensive gauze bandage liner 76 and a gas cartridge 34 hidden in the pouch 78 at a bottom edge. Elongated hook strap 80 and loop strap 82 extend diametrically from the bottom edge for securing the dome-shaped pressure bandage 70 to a head injury. The straps 80, 82 can optionally be made integral with the production of the elastic bladder 74 or attached by adhesive.

Thus, various pressure bandages have been shown applicable by even the injured at the time of need.

It is to be understood that the present invention is not limited to the embodiments described above, but encompasses any and all embodiments within the scope of the following claims.

We claim:

1. A pressure bandage for a wound comprising:
   a flexible, elliptical-shaped bladder having an inner surface and an outer surface;
   a plastic strip extending longitudinally along the inner surface of said bladder;
   a dressing configured to slide along said plastic strip to adjust to the location of the wound; and
   a pressurized gas container attached at one edge of the flexible bladder;
   whereby the bladder and dressing can be positioned over the wound, and the pressurized gas released to inflate the bladder to press the dressing against the wound to suppress bleeding.

2. The pressure bandage for a wound according to claim 1, wherein the pressurized gas container is maintained in a pouch.

3. The pressure bandage for a wound according to claim 2, wherein a strap with a loop fastener patch extends from one end of the bladder for attachment with a hook fastener patch on the opposite end of the bladder.

4. The pressure bandage for a wound according to claim 3, wherein an adhesive strip is located on the opposite end of the bladder for initial attachment to the wound area.

* * * * *